United States Patent [19]

Chachowski et al.

[11] Patent Number: 5,650,068
[45] Date of Patent: Jul. 22, 1997

[54] COLUMN AGGLUTINATION ASSAY AND DEVICE USING BIPHASIC CENTRIFUGATION

[75] Inventors: Rosemary K. Chachowski, Manville; Thomas M. Setcavage; Kathleen J. Reis, both of Milford, all of N.J.

[73] Assignee: Ortho Diagnostic Systems Inc., Raritan, N.J.

[21] Appl. No.: 632,974

[22] Filed: Apr. 16, 1996

Related U.S. Application Data

[63] Continuation of Ser. No. 112,402, Aug. 26, 1993, Pat. No. 5,552,064, which is a continuation of Ser. No. 23,500, Feb. 26, 1993, abandoned.

[51] Int. Cl.⁶ .......................... B01D 37/00; B01D 21/26
[52] U.S. Cl. .......................... 210/518; 210/359; 422/101; 422/72; 435/7.1; 436/177; 436/178
[58] Field of Search .......................... 210/359, 198.1, 210/518, 781, 782, 787; 422/72, 101; 435/7.1, 2; 436/177, 178

[56] References Cited

U.S. PATENT DOCUMENTS

| | | |
|---|---|---|
| 3,586,064 | 6/1971 | Brown et al. |
| 3,799,342 | 3/1974 | Greenspan. |
| 3,932,277 | 1/1976 | McDermott et al. |
| 4,035,294 | 7/1977 | Landers et al. |
| 4,140,662 | 2/1979 | Reckel et al. |
| 4,244,694 | 1/1981 | Farina et al. ............................. 422/72 |
| 4,435,293 | 3/1984 | Graham, Jr. et al. |

FOREIGN PATENT DOCUMENTS

| | | |
|---|---|---|
| 0104881 | 4/1984 | European Pat. Off. |
| 0305337 | 3/1989 | European Pat. Off. |
| 0194212 | 5/1990 | European Pat. Off. |
| 0485228A1 | 5/1992 | European Pat. Off. |
| 2660437 | 3/1990 | France. |

*Primary Examiner*—David A. Reifsnyder

[57] ABSTRACT

The present invention provides a method and device for detecting the presence of binding ligands, especially blood group antigens or antibodies thereto, which utilize a matrix of substantially noncompressable microparticles, which matrix provides superior performance in allowing movement of nonagglutinated reactants, especially red blood cells, while constraining, preferably in a so-called "band formation" agglutinated reactants, especially red blood cells. The device of the invention further comprises a chamber the transverse cross-sectional shape thereof being an ellipse, or preferably a flattened ellipse with two sides parallel to the longitudinal axis.

1 Claim, 4 Drawing Sheets

COLUMN AGGLUTINATION ASSAY AND DEVICE USING BIPHASIC CENTRIFUGATION

This is a division of application Ser. No. 08/112,402, filed Aug. 26, 1993, now U.S. Pat. No. 5,552,064 which is a continuation of application Ser. No. 08/023,500 filed Feb. 26, 1993 now abandoned both of which are hereby incorporated by reference.

BACKGROUND OF THE INVENTION

This invention relates to the field of agglutination assays to detect the binding of ligands, and particularly immunological binding (antigen and antibody binding) such as that involved in blood group serology ("immunohematology").

Blood group serology requires the determination of blood cell compatibility between a blood donor and a patient recipient before a transfusion or organ transplant involving the patient. Blood cell compatibility is determined by the non-occurrence of an immunological reaction between antibodies contained in the blood serum of a patient and antigens present on blood cells from the donor.

Many different blood group antigens are found on the surface of the red blood cells of every individual. These antigens, the products of inherited genes, exist in a unique combination in everyone except identical twins. Blood grouping is generally the process of testing red cells to determine which antigens are present and which are absent, normally utilizing antibodies to the antigen tested for.

Additionally, when a person does not have a particular red cell antigen on his red blood cells, his or her serum may contain an antibody to that antigen. Whether or not the antibody is present in the serum depends on whether the person's immune system has been previously challenged by, and responded to, that specific antigen or something very similar to it. For example, a person whose red blood cells are Type A, i.e., having "A" antigens on the red cells, will have anti-B antibodies in his or her serum. Thus, if such a person is given type B blood, an immunological reaction will occur with possible serious clinical consequences.

As an additional consideration, it should be noted that the human body is constantly exposed to antigens in pollens, food, bacteria and viruses. Some of these "natural" antigens are apparently so similar to human blood group antigens that they stimulate almost every susceptible person to produce antibodies. Thus, certain antibodies are expected in the serum of anyone whose red cells lack the reciprocal antigen. This is especially true of the ABO system. Accordingly, a second confirmatory test is often performed on the patient/donor sera. The test for expected antibodies of the ABO blood group system in sera is called "reverse" blood grouping.

Antibodies of the ABO blood grouping system are generally immunoglobulin M (IgM). These antibodies have ten antigen binding sites per molecule. The IgM antibody is large enough to span the distance between red blood cells, so that when they are centrifuged, the cells will be bound together in a lattice "cell-antibody-cell-antibody" and will remain clumped together in agglutinates. For example, if anti-A is added to blood group A or blood group AB cells and the mixture is centrifuged, the cells will remain in clumps when resuspended. With the same antibody, group O and group B cells will resuspend as individual cells. Agglutination caused by one antibody, such as an IgM antibody, is called direct agglutination.

The anti-Rh blood group reactions tend to give weaker agglutination which can be enhanced by the addition of high molecular weight polymers. Some anti-Rh antisera consist of immunoglobulin G (IgG) antibodies and will cause direct agglutination, if facilitated by the presence of high protein concentrations, such as 25% bovine albumin (often found in commercial anti-D reagent preparations).

Such facilitation is needed as IgG cannot easily span the distance between cells which tend to repel each other. Thus, it will bind to red cell antigens matching its specificity, but will not agglutinate such red cells as effectively as the larger IgM antibodies will. The presence of IgG antibody bound to a red cell is thus usually detected by the addition of anti-IgG which will cause the requisite agglutination, resulting in a lattice of "red cell-IgG/Anti-IgG/IgG-red cell".

Serum naturally contains IgG that will neutralize the anti-IgG antibody added to bind to red blood cells. Therefore, the serum must be removed before such anti-IgG is added to the cells. Tests for IgG bound to red cells in vivo are called direct antiglobulin tests. Tests for IgG bound to red cells in vitro are called indirect antiglobulin tests. Such antiglobulin tests are also called "Coombs" tests.

It is standard bloodbanking practice to test for A, B and D ($RH_o$) antigens on a sample of a person's blood (and to perform tests for other antigens in selected cases), and to crosscheck the results by testing the person's sera to determine the acquired antibodies that might be present. The former is referred to as "forward typing", while the latter is referred to as "reverse typing". The results from each of these typing exercises have to agree.

Since the early 1900's, the general approach, known as the "Landsteiner" method, has been to add a patient's red blood cells to a standard laboratory test tube containing a blood group antibody (such as Anti-A or Anti- B), mix to allow antibody/antigen binding reactions to take place, and then to centrifuge. If the antigen tested for is present, the antibody/antigen binding will have taken place resulting in agglutination of the patient's red blood cells. The test tube is manually shaken to dislodge the centrifuged button of "clumped" cells at the bottom. A subjective determination is then made as to whether or not the dislodged cells are "clumped", and to what extent.

During the mid-1900's, attempts were made to simplify this technique to minimize the subjective nature of the test and to reduce mistakes. It was recognized that a somewhat permanent record of the results of compatibility testing could be had by employing wettable, either non-absorbent, or in some cases absorbent, test slides or test cards having the requisite immunochemical reagents on at least a portion of their surfaces. U.S. Pat. Nos. 2,770,572, 2,850,430, 3,074,853, 3,272,319, 3,424,558, 3,502,437 and 3,666,421, and European Patent Application # 0 104 881-A2 depict select examples of such test cards and related apparti.

More recently, techniques to increase the sensitivity and accuracy of certain antiglobulin testing, such as the so-called "Coombs" test, have been developed. U.S. Pat. No. 4,435, 293 to Graham et al. describes a bloodtyping system (Simwash®) which uses a system of test tubes that eliminates the washing steps of the original Coomb's method, as the Simwash® system provides "self-washing" of the red blood cells. Antiglobulin tests, such as that just described, require that the red blood cells be free of their serum, which contains unbound IgG antibodies. With the Simwash® system, the dense cells are centrifuged into a column, while the less dense serum remains at the top.

European Patent Application # 0 194 212 describes a blood compatibility testing system using gel in a column, such gel being in particular, Sephadex® which is a 3-dimensional network or matrix of dextran chains cross-linked with epichlorhydrin (product of Pharmacia Fine Chemicals, Uppsala, Sweden and Piscataway, N.J.), that catches agglutinated red blood cells and allows unagglutinated cells to pass through to the bottom.

One of the drawbacks in the use of the last-mentioned system, and especially in the manufacture of such a test system using gel as a medium, is that gels such as Sephadex® have to be settled prior to insertion into a test tube to get rid of the so-called "fines", which are contaminating small molecular weight compounds or fragments that may interfere with the separation capacity of the gel. Gel fines have historically been known to clog chromatographic separation columns.

A gel also has to be swelled prior to use and in order to accurately calculate the amount of reagents to be used in conjunction with the test system. Calculations of requisite amounts of reagents, buffers and the like have to take into account the gel swelling dilution factor. Additionally, some of the reagent is lost as it is absorbed by the porous gel and not available for binding to the analyte tested for. Greater quantities of reagent must be added to compensate for this loss. The gel is also inherently more fragile to mechanical handling, and can break apart during the swelling process, causing an uncontrollable variation in gel particle size.

Another drawback one suffers in the use of Sephadex® is that it is very fragile to temperature extremes, and tends to dry out or break apart, causing stability, shipping and storage problems, which include shrinkage, and concurrent alterations in test properties. The breakage can result in such above-mentioned fines that alter or restrict the normal flow of the blood cells through the material. An additional shipping and storage problem is occasioned by the inability to freeze Sephadex®-containing test devices.

SUMMARY OF THE INVENTION

The present invention provides a method and device for detecting the presence of binding ligands, especially blood group antigens or antibodies, which utilize a matrix of substantially noncompressable microparticles, which matrix provides superior performance in allowing movement of nonagglutinated reactants, especially red blood cells, while constraining, preferably in a so-called "band formation" agglutinated reactants, especially red blood cells.

In a preferred embodiment, the device of the invention is a substantially transparent elongate container which has disposed therein, a matrix of substantially noncompressable microparticles, which matrix is provided in a quantity and positioned within said container in such a manner so as to allow detection of the presence or absence of agglutinated reactants. The microparticles may be impregnated with or immersed in a reagent to detect binding ligands such as blood group antigens or antibodies, prior to the addition of the matrix to the device. Alternatively, a liquid form of such a reagent may be added to the opening of the container so that it may filter through the microparticles contained therein. A liquid sample possibly containing an analyte of interest that will bind to the reagent and cause an agglutination reaction is also added to the container, either concurrently with the mentioned reagent, or subsequent to the addition of the reagent. The container is centrifuged and the presence or absence of agglutinates detected.

DETAILED DESCRIPTION OF THE INVENTION

The following is a more detailed description of certain key aspects of the invention. The preferred device of the invention is generally a container, or elongate substantially transparent hollow member, having at least one open end, sometimes referred to herein as an inlet port. By inlet port is meant an area to which samples and/or reagents, buffers, and the like may be applied to eventually achieve contact with the matrix of the invention. In some embodiments, the elongate member has a substantially closed end, opposite the inlet port. By substantially closed end is meant closed to such an extent that the matrix is retained within the member, and does not spill out, and reactants one wishes to retain in the matrix are also retained. By elongate is meant a container that is somewhat longer in proportion to its width and aligned along a longitudinal axis. The matrix of the invention is thus housed in a somewhat columnar fashion so that reactants may move through its length if nonagglutinated, and be caught by the matrix if agglutinated. A container shape that is long enough in the area that houses the matrix to allow this separation and detection thereof, will be suitable for the purposes of the invention, it being understood that the remaining aspects of the container shape may differ considerably. The area of the hollow member or container that houses the matrix is generally referred to herein as the "agglutinate detection zone."

The overall shape of the container should, in general, facilitate this separation process. For example, in preferred embodiments, the entire container is basically of a laboratory test tube shape, including those test tubes that may be described as "cone-shaped" in their entirety or a portion thereof. In a further preferred embodiment, the device of the instant invention contains a chamber which is narrowed in one transverse cross-sectional dimension with respect to the other, so that the thickness of the gel matrix is reduced. The transverse cross-sectional shape of the separation region of the chamber is thus an ellipse, or preferably a flattened ellipse with two sides parallel to the long axis, rather than a circle. Other preferred embodiments include those configurations wherein only a portion of the container is cone-shaped, (e.g.: in the area that contains the matrix). In this case, the cone-shaped area may be joined to a sample-receiving area that is of a shape suitable to contain the samples or reagents as added by the user, and may be rounded, cuboidal, and the like in configuration. By way of example only, FIGS. 1–4 depict various shapes and configurations of portions of devices for carrying out the method of the invention.

Figures 2, 3:
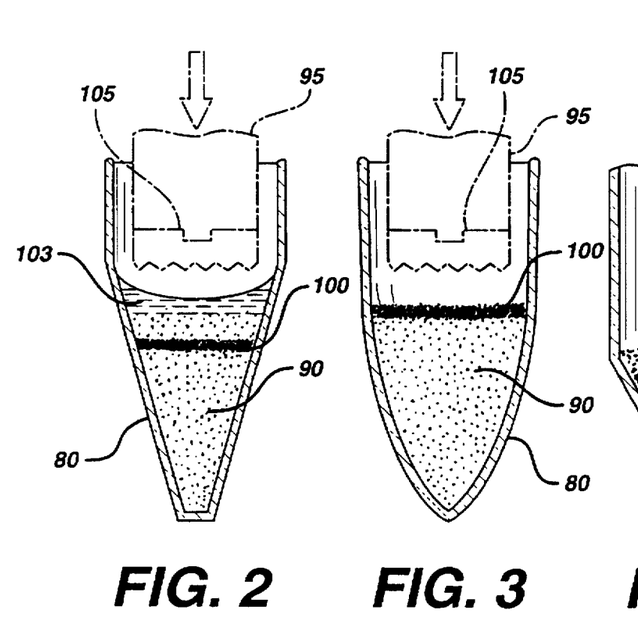
FIG. 2 is a cross-sectional view of a test-tube column agglutination device.
FIG. 3 is a cross-sectional view of another embodiment of a test-tube column agglutination device.
Figure 4:
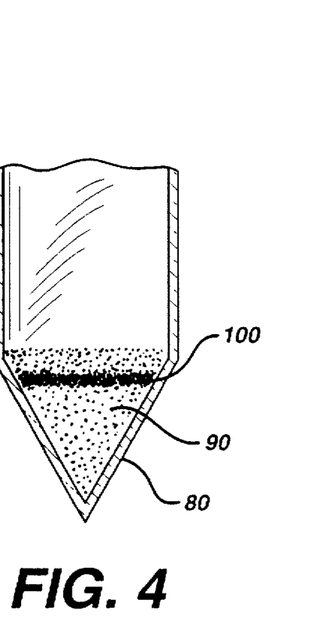
FIG. 4 is a cross-sectional view of a third embodiment of a test-tube column agglutination device.

A housing having two separate areas, each defined by its relevant shape, provides the additional advantage of an "upper" chamber for incubation of cells and serum prior to movement of this mixture through the matrix. This is especially true when the juncture between this upper chamber (sample-receiving area), and the agglutination detection zone (or area just above it) is defined by an opening that is smaller than the opening to which samples and reagents are applied (the latter being the inlet port area). This is because the larger inlet port opening facilitates the adding of cells and serum, while the smaller opening prevents their passage through the matrix until the user applies a force such as centrifugation, to effect their movement. The user may therefore exert control over the timing of the agglutination assay. FIGS. 2 and 3 illustrate this concept. FIG. 2 depicts a housing 80 with an upper chamber 95 disposed therein for receiving samples, said upper chamber having an opening 105 which will not permit movement of samples applied to the upper chamber until the user effects that movement in an appropriate manner. FIG. 2 also depicts an "initial reaction zone" 103 containing buffer or a reagent for the binding and agglutination steps of the assay. A band of agglutinated reactants 100 is formed within the matrix 90. FIG. 3 is an alternate embodiment which lacks the initial reaction zone. In this embodiment, the binding reaction may have been performed prior to addition of the reactants to the device, with the matrix acting as a filter for the agglutinates. Alternatively, the reactants may have been added directly to the upper chamber and allowed to react for a time prior to centrifugation and passage to the matrix below. The agglutinates are then caught on top of or in the matrix, after centrifugation through the opening 105. FIG. 4 depicts yet another configuration for the agglutination detection zone of the device, and also depicts formation of the band 100 within the matrix rather than on top of the matrix.

By "substantially transparent" is meant any material that is translucent or transparent to such a degree that the presence or absence of agglutinates may be readily ascertained either by the naked eye, or through the use of detecting instrumentation for that purpose. The device may be substantially transparent in its entirety or only in selected areas, as for example, the area of agglutinate band formation in a positive sample. It is within the contemplation of the invention that observation of positive and negative agglutination reactions may be made with an instrument designed to optically or otherwise detect cluster agglutinate and/or band or button formation within a certain area of the agglutination reaction zone. This observation process may be performed manually with the instrument, or it may be a so-called "user walk-away" automated observation process.

Figure 1:
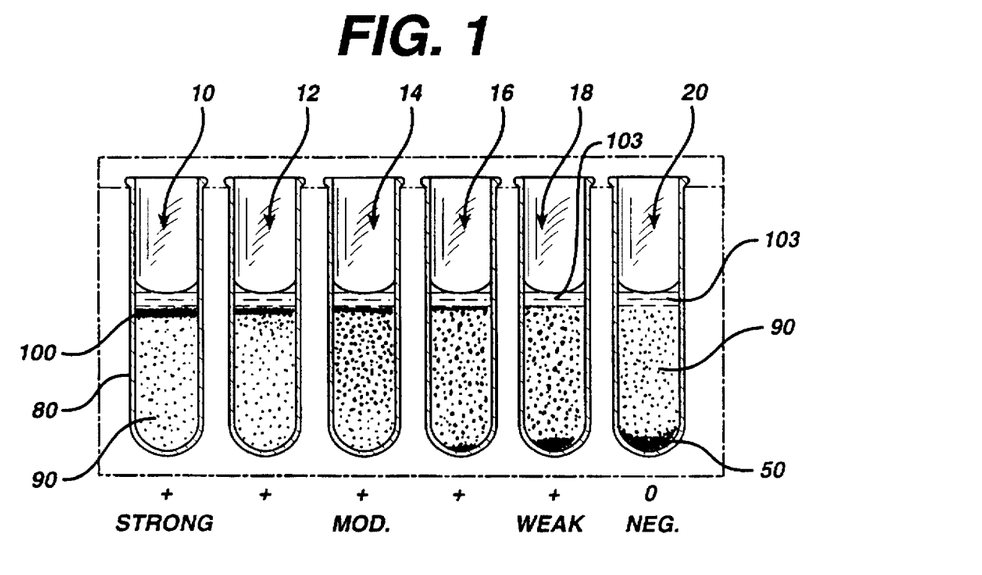
FIG. 1 is a cross-sectional view of a rectangular-shaped test tube cartridge containing several cartridges used for column agglutination assay.

Containers such as laboratory test tubes and columns generally known to the art of immunoassay and bloodbanking may be used for the purposes of carrying out the method of the invention, as long as they are adapted to centrifugation and instrumental observation, if desired. Suitable containers may comprise materials such as glass, polystyrene, polyethylenes, polypropylene, polycarbonates and the like. Preferred is the test tube cartridge, which is generally a premolded rectangular-shaped cartridge containing several tubes. FIG. 1 depicts one embodiment of such a cartridge. Especially preferred are the dual chamber laboratory test tubes such as those described previously, particularly if such test tubes are in cartridge form and adapted to be filled with reagents, buffers, matrix, and the like with automatic pipetting devices, during the manufacturing of the devices or later when the devices are used to conduct assays.

The matrix of the invention comprises substantially noncompressable microparticles. By "substantially noncompressable" is meant resistant to change in shape or size that may be caused by the exertion of force to the matrix, such as centrifugal force, magnetic force, electrical force, hydrostatic pressure, force by negative or positive pressure, and the like, or storage for long periods of time with normal gravitational force. The particles may be of any shape as long as the movement of unagglutinated reactants is not impeded by irregularities, and so on. The size of the particles may vary considerably according to the particular binding ligands involved in the agglutination assay. One skilled in the art will understand that agglutinated reactants should be retained in or on top of the matrix while non-agglutinated reactants travel the matrix to the bottom or outside of the device altogether. However, in the case of agglutination of red blood cells, preferable matrix microparticle size ranges are generally from about 50 microns to about 300 microns, and more preferably about 50 microns to about 200 microns, and most preferably about 50 microns to about 150 microns.

Suitable noncompressable materials for use herein comprise various silicon dioxide compounds, including glass and sand, metal compounds as long as they are light enough in color to permit visual observation of agglutination if desired, various plastic compounds, and the like. Exemplary of the above materials are such commercially available polystyrene beads as those that may be obtained from Polysciences, Inc.; sea sand, available from Fischer or Mallinkrodt; cellulose particles, such as those available from Whatman; and glass beads such as those available from Jaygo Incorporated (from Dragonite) and Hüls Petrach Systems. More particular examples of these are set forth in the experimental example section of this specification.

The matrix as described above is provided in the agglutinate detection zone of the device of the invention. If the device is columnar in shape, the matrix is most often provided along its length proximate to the closed end. However, in some embodiments, the matrix is provided only throughout a "middle" portion of the device, and may even, in some embodiments, rest on top of a second material serving as a plug, such as a glass fiber or other type of fiber. The devices may also interface with instrumentation at one or more locations. For example, the inlet port may be joined to an instrument, such as a pipetting device to receive samples therethrough. The device may interface with instrumentation designed to effect movement of the reactants, for example, to push or to pull them through the matrix. In some embodiments, a vacuum may be applied to pull reagent liquid and even nonagglutinates through the device, while agglutinates are retained within or on top of the matrix. In other embodiments, instrumentation may interface with a portion of the device to apply a force, such as a liquid stream, to move the reactants through the matrix.

Prior to adding the matrix microparticles to this zone, they may be first washed in any appropriate manner to remove undesirable contaminants, and to avoid nonspecific binding. The particles may be added to the device in a slurry consisting of particles in antiserum, buffer, or other desired reagents or diluents, whether alone or in combination. The particles may also be added to this zone in a dry form, and antisera, appropriate buffers and the like added subsequently, if desired. In preferred embodiments, the microparticles are completely immersed in an appropriate reaction solution or buffer within the agglutinate detection zone of the housing, and a layer of the solution alone extends from a top portion of the matrix. This extended area is referred to as the "initial reaction zone", and in columnar devices other than the dual chamber devices, is an area wherein reactants may first come into contact with each other, mix and begin to react.

By way of illustration, the column agglutination method of the invention will be described in the context of certain bloodtyping and compatibility procedures. A forward bloodtyping assay may be conducted utilizing the column agglutination device as herein described by using a columnar device to which has been added the matrix of the invention. A monoclonal antibody or polyclonal antibody containing antiserum is dispersed in a physiologically compatible buffer and added to the matrix of microparticles to immerse them, and extends from the matrix toward the inlet port to form the initial reaction zone. Suitable amounts of such antibodies may be routinely optimized by those skilled in the art, depending generally on the antigenic affinity and specificity of the antibodies. The antibodies are dispersed in a buffer that may also contain suitable additives known to the art to help potentiate their reactivity and prevent nonspecific binding, such as high molecular weight polymers, and the like. Examples of these include polyvinyls, dextran, gelatin, and polyethylene glycol. Lower molecular weight polymers may also be added to increase the density of the solution.

To the initial reaction zone is added a saline suspension of a patient's red blood cells. Those skilled in the art will readily ascertain that a suitable suspension of cells is about 2–6%, and preferably about 2–3%. If the suspension is too dilute, any resulting agglutination reaction will be difficult to read. If the suspension is too concentrated, the system will be overloaded and agglutination indistinguishable. The binding reaction is allowed to take place and then movement of the reactants to and through the matrix is effected. This movement is generally effected by exerting a force, such as those forces described above. In certain preferred embodiments, a centrifuged force, negative pressure, or a hydrostatic force is applied.

If centrifugation is the technique utilized to exert force on the reaction mixture to effect its movement onto or through the matrix, then one skilled in the art will appreciate that centrifugation times and speeds may vary greatly for optimal results. In preferred embodiments, centrifugation should be at a speed and for a time suitable to allow the agglutinates, if any, to form a cluster or band near the top portion of the matrix column, rendering a clearly observable positive reading, while the non-agglutinated negative cells travel to the bottom of the device to form a button. If the device is spun for too long or at a speed that is too high, the agglutinates will be forced to the bottom of the tube. It is also desirable that a centrifuge with a swing-out head be utilized to ensure that the reactants travel somewhat through the center of the matrix area, and do not lie on the side of the device.

In this illustration, if antibodies to Type B blood cells were added, Type B blood cells contained in the patient's sample will bind to the antibody, forming a line of aggregated cells trapped near the top portion of the matrix. Type A cells will not agglutinate, and will be spun to the bottom of the device. Often times, a patient's cells may contain weakly reacting variants. The moderate reaction might be demonstrated by smaller scattered agglutinates throughout the column matrix, while negatives form a button on the bottom of the matrix column. FIG. 1 demonstrates examples of reaction end-points that may be observed using the method and device of the invention. Tube 10 demonstrates a strong positive reaction, with a firm band 100 of agglutinates. Tube 12 shows a positive reaction that is somewhat weaker than the previous, as the agglutinated band has broken apart into smaller agglutinates. Tube 14 demonstrates a more moderate positive reaction with a smaller agglutinates distributed throughout the middle portion of the matrix, and even settling to some extent on the bottom, as in tube 16. Tube 18 depicts a very weak positive reaction, with most of the cells collected on the bottom. Tube 20 shows a clear negative, with a button of cells 50 on the bottom of the tube, and no agglutinates dispersed within the matrix 90.

The device and method of the invention may be utilized for direct agglutination studies of the kind just described for the detection of many different blood cells including white blood cells, platelets, red blood cells, and the like. If visual observation of agglutinates is desired, it is preferable to first stain any colorless cells or colorless particles adhering to cells with a dye suitable to effect a visually perceptible agglutination reaction. The hemoglobin red blood cells provides such a suitable color naturally, without staining. Direct agglutination studies may be performed on ABO red blood cells as illustrated above, as well as those blood cells containing D, C, c, E, e, K antigens, and the like. Similarly, when sera are to be tested for the presence of antibodies to a particular antigen or cell containing an antigen, they can be mixed with known antigens. If the unknown serum contains antibodies to the known antigen that is provided, the reactants will be agglutinated and trapped when they move onto or down through the matrix, while negative serum will not effect a reaction, and agglutinates will not be trapped. It is preferred to utilize a dual chamber configuration in conducting these last-mentioned assays to allow the known antigen or cells containing antigen to incubate with the patients' serum prior to movement of the mixture onto or through the matrix by centrifugation, or other appropriate means.

In the context of immunohematology applications of the device and method of the invention, a patients' serum may also be screened for unexpected antibodies in the manner described above, such as the Kell, Duffy and Kidd antigens. Antiglobulin tests such as the Coombs Test may also be performed. In Coombs' testing, the cells should be free of serum containing unbound antibodies. With the system herein described, the dense cells are centrifuged into the column. The less dense serum remains at the top of the column similar to the process disclosed in U. S. Pat. No. 4,435,293. Anti-IgG dispersed within the matrix will agglutinate cells which have IgG antibodies bound to their antigens, and the agglutinates will be trapped on top of or in the matrix. Cells which have no IgG bound will travel through the column to the bottom of the tube.

The device and method of the invention have been illustrated in great detail for use in a blood serology context. However, it should be understood that it is within the contemplation of the invention to conduct binding assays involving any binding ligands associated with particles, such that the particles will agglutinate as a result of the binding of the ligands to their binding partners. For example, any binding ligand that could be attached to a particle or other carrier that takes the place of the red blood cells (bearing antigens) might be suitable. The particles serve as carriers for these ligands just as the red blood cell "carries" its antigen. Examples of other ligands include specific binding proteins disclosed in Reissue Patent #31,006 to Schuurs et al, herein incorporated by reference insofar as its disclosure of binding ligands is concerned. Such particles might be inert carriers such as those disclosed in U.S. Pat. No. 4,140,662, which is herein incorporated by reference. Suitable carrier particle size and composition will vary according to the binding ligands one seeks to detect, examples of which are disclosed in the referenced patent. Suitable matrix microparticle size and composition will also vary in accordance with the selected carrier particles and binding ligands. The examples section of this specification provides guidance in techniques useful to determine optimal particle size and composition. Although red blood cell agglutination system is illustrated, one skilled in the art will appreciate that other systems may be optimized in this manner. In some embodiments, it is preferable that the particles be colored, to enable a visual observation of agglutinated clumps or bands of particles, similar to the effect obtained with the visually colorful red blood cells.

The claimed device and method avoid the drawbacks associated with devices and methods known in the art of agglutination assays, by providing an assay system that utilizes a matrix of substantially noncompressable microparticles. Such particles do not have to be "swelled" prior to use in this system and prior to calculation of amounts of reagents to be added. The particles are less porous than other matrices known to the art, and accordingly, do not absorb a great deal of any reagents that might be added, which renders more of the reagent available for reaction. Also, variation in particle size is minimal, as a great deal less breakage occurs. Surprisingly, the assay system of the invention requires less centrifugation time, when centrifugation is employed to move the reactants through the matrix.

These factors, inter alia, result in an assay system that tends to require less reagent and is therefore quite cost effective. Additionally, the system provides the added advantage of greater storage and shipping capabilities. For example, if the devices happen to turn upside down in the shipping or storage phase, the matrix may be easily tapped back into place within the support member. Also, the devices containing the matrix of the invention may be stored in a frozen state, 15° C., or room temperature, without stability problems.

Figure 5:
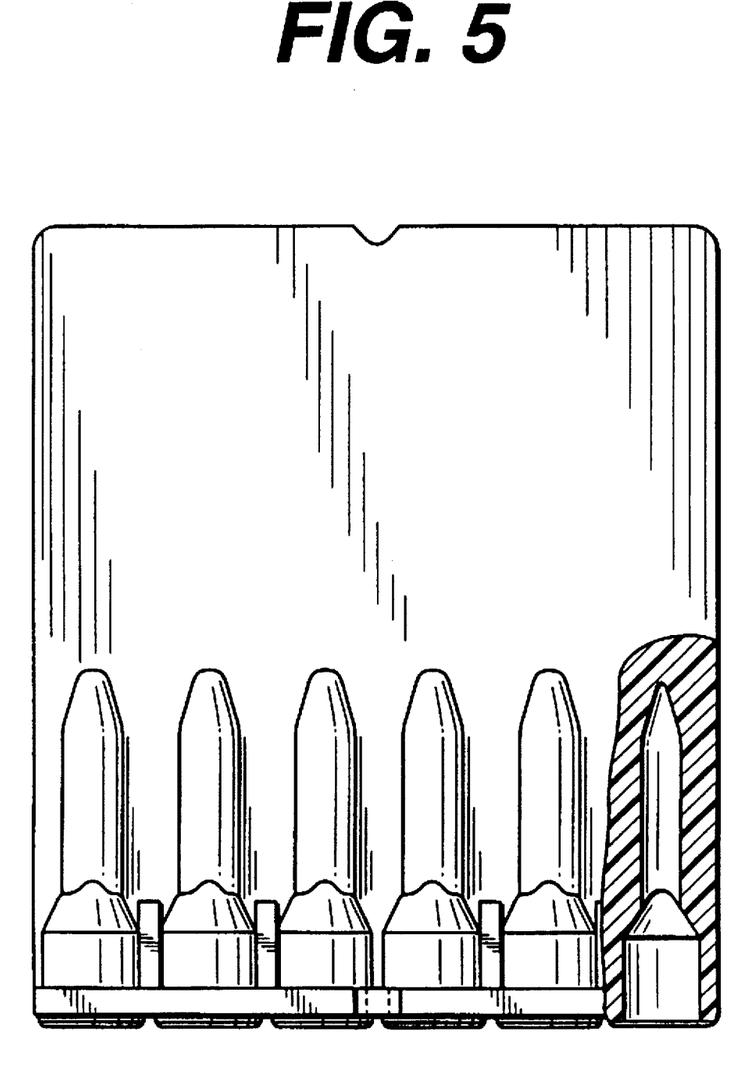
FIG. 5 is a front view of a six-column cassette used for column agglutination assays.
Figure 6:
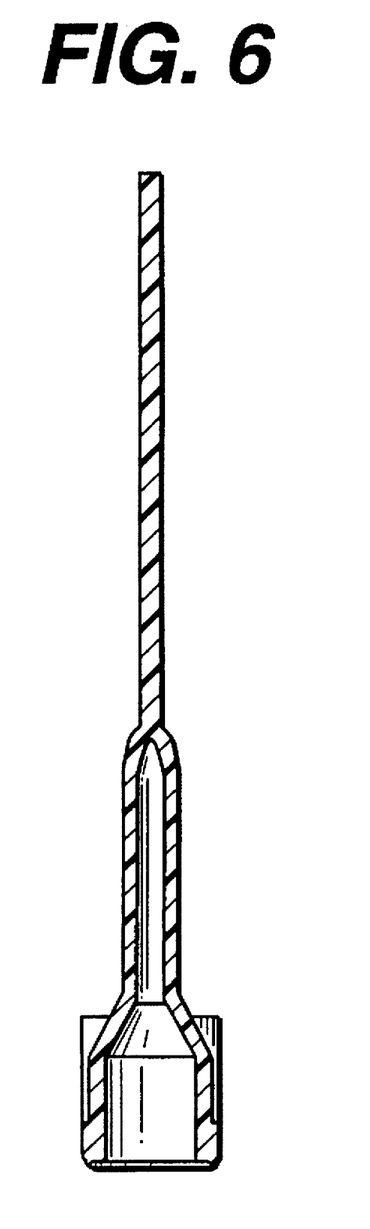
FIG. 6 is a side view of a cassette containing six columns for agglutination assays.
Figure 7:
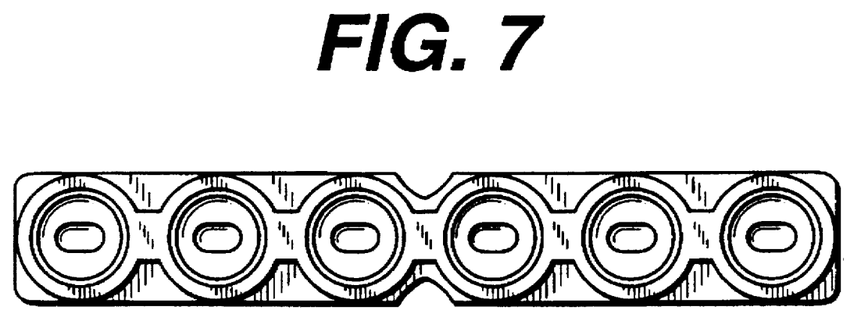
FIG. 7 is a top view of a six-column cassette used for column agglutination assays.

Applicants have identified a problem with reading the instant cassettes, in what they have termed "sidedness". That is, the reaction of agglutination of red cells is often visible within the gel matrix only on one side of the cassette chamber and not the other. To overcome this problem, Applicants have in a further embodiment of the invention, described a chamber wherein the separation region of the chamber is narrowed in one transverse cross-sectional dimension with respect to the other, so that the thickness of the gel matrix is reduced. This is accomplished without reducing the total volume of the chamber. Thus, the transverse cross-sectional shape of the chamber is an ellipse, or preferably a flattened ellipse with two sides parallel to the long axis, rather than a circle. This aspect of the invention is best appreciated with reference to FIGS. 5–7. FIG. 5 depicts a cassette having six columns. FIG. 6 depicts the cassette viewed from the side, longitudinally. FIG. 7 depicts the cassette viewed from above, transversely; this Figure furthermore depicts the elliptical or flattened elliptical shape of the interior of the column. That is, the interior transverse shape of the columns is not circular but oval or elliptical. When the chamber is viewed along the transverse cross-sectional dimension, the chamber and matrix are thin enough that red cells and agglutinates on the opposite side of the chamber are visible.

The following specific examples exemplify the invention, but should not be considered as limitative thereof:

I. MICROPARTICLE SELECTION

The following experiments depict a selection of substances which will allow unagglutinated red cells to pass through a column when centrifuged, while agglutinated red cells are trapped either on top of or in the column. The general methods for conducting the following experiments were:

1. particles added to a container, such as a test tube;
2. red blood cells under test are mixed with reagent containing antibodies and then deposited onto matrix of particles;
3. the tubes are centrifuged in a centrifuge capable of spinning containers horizontally;
4. The tubes are observed for agglutination/nonagglutination.

EXAMPLE 1

Testing Various Particles:

Small plastic tubes were prepared with about ½ ml microcellulose (Whatman Microcellulose DE32, DE52, QA52, SE52 (prefixes indicate different charges)). (volume is packed volume—from slurry made in phosphate buffered saline (PBS))

Results:

DE32/cells do not pass through

DE52/some cells in top ½ of tube, others pass to bottom

Resuspended in anti-human globulin (AHG); then added IgG coated cells. (Ortho Coombs Control Cell™ e.g. OCC)

Control and negative cell (Selectogen™)

DE52

QA52 All negative cells passed to the bottom

SE52

Tested Aerosil=approximately 740 nm diameter silicon dioxide particles and

Dow 0.8 µ polystyrene latex particles

Cells did not go through these suspensions even after a hard spin.

Discussion:

Human red cells (7 µ diameter) can be centrifuged through a bed of particles of 100–150 µ.

EXAMPLE 2

Tested additional particles in test tube cartridge: Cellulose particle sizes are much larger (≈100–150 µ) than red cells (7.0µ).

| 1. Cellulose Whatman C F11 | fibrous cellulose powder |
| 2. Cellulose Whatman C F31 | microgranular |
| 3. acid washed glass beads | less than 150µ |
| | 150–212µ |
| | 425–600µ |

Procedure:

(1) Particles are suspended in Ortho Bioclone Anti-A™ lot # BAA 1100

(2) Suspension loaded into upper portion of device.

(3) Centrifuged lightly—cellulose stuck in top.
Plug broken with probe and respun to load cellulose in bottom.
The glass beads may be loaded dry and liquid added.

(4) 10 ml Affirmagen™ A cells or B cells were added (5) Centrifuged in a table-top swing-out head centrifuge (Sorvall GLC-1 microtiter plate carrier). 900 RPM for short periods to find time required for B cell to reach bottom.

|           | 30' |   | Plus 1 min. |   | Plus 1 min. |   | Plus 5 min |   |
|-----------|-----|---|-------------|---|-------------|---|------------|---|
|           | −   | + | −           | + | −           | + | −          | + |
| Cellulose 1 | T | T | ½ | T | ½ | T | ½ | T |
| Cellulose 2 | T | T | T | T | T | T | ⅒ | T |
| Beads (S) 3 | part | T | B | T | B | T | B | T |
| Beads (M) 4 | part | T | B | T | B | T | B | T |
| Beads (L) 5 | part | T | B | T | B | T | B | T |

T = cells on top
B = cells on bottom
Part of fraction refers to cells on bottom.

All sizes of glass beads tested worked very well for typing A cells- spin time between about 30–90 seconds.

Tried large bead (425–600 μ) in commercial anti-IgG with a strongly coated cell (Ortho Coombs Control Cell™ (OCC)) and an uncoated cell (Affirmagen™ A cell)

25 μl AB serum; 10 μl cell suspension; spun 1 minute 900 rpm.

Separation of cells from serum allowed antiglobulin to agglutinate cells. Agglutinates were trapped in the column of beads.

Discussion:

The above section B studies were a continuation of the selection of particles which will allow unagglutinated cells to be centrifuged through while trapping agglutinated cells. Two cellulose powders and three glass bead sizes were tested. They were each suspended in commercial blood grouping serum Anti-A. Red cells of blood group A or B were added and carefully centrifuged through the columns of particles being tested.

Tests for IgG antibodies in human serum are preferably performed with the indicator cells separated from the test serum, since the serum contains relatively large amounts of IgG which would neutralize the reagent anti-IgG. Cells known to be coated with IgG antibodies were mixed with group AB serum known not to contain antibodies to the cells. Cells known to be not coated with antibodies were tested as a control. The mixtures were added to the top of columns of glass beads in commercial anti-IgG reagent then centrifuged.

Results:

Some but not all of the negative cells were centrifuged through the cellulose particles. The agglutinated cells remained on top of the column. All of the negative cells were at the bottom of the glass bead columns and all of the positive cells remained at the top.

Cells coated with IgG antibodies were agglutinated by the Anti-IgG trapped in the column of beads. Cells not coated with IgG antibodies were not agglutinated and were at the bottom of the column. There was a marked difference seen between negative and positive examples when anti-IgG was used.

The test sera and cells used for these experiments were selected as those which give strong reactions. The glass beads provided support for agglutinated A cells and unagglutinated B cells were easily spun through the columns. The antibody coated cells were separated from the serum in which they were suspended at least well enough to detect strong reactions. Serum remains in the upper portion of the column and does not neutralize the anti-IgG.

EXAMPLE 3

Additional Particles:

Iron metal filings, ≈40 mesh obtained from Fisher 157-500. Sea Sand, washed; obtained from Fisher-S25-500, lot 901223 Sea Sand, washed; and dried; obtained from Mallinkrodt 7062—lot 7062 KED2.

1. Added 5 to 7 mm of particles under test to each of 2 columns in a test tube cassette.
2. Added Ortho Bioclone Anti-A™, lot BAA110D to each column, mixed to get air pocket out. Iron filings packed in such a manner that the needle used for stirring would not go through the filings or down the side. Some bubbles of air remained in the bottom of the tube.
3. Added 10 μl of cells to each (Ortho Affirmagen Anti-A™, lot #A844). A cell is positive and B cell is negative with Anti-A.
4. Centrifuged for ≈8 min. in table-top swing-out head centrifuge.

Results:

Iron filings look black, cannot see red cells. Need to use filings that will be more appropriate as a background color for the color of test particles under study (i.e.: red cells). Fisher sand and Mallinkrodt sand both held agglutinates on top, both sands allowed the negative cells to pass through to the bottom.

Mallindkrodt sand was whiter and provided a superior background color for assessing a negative reaction.

Discussion:

In the above section C studies, additional solid particles were screened to find alternative support media. Iron metal filings and two sources of sea sand were tested using blood grouping serum anti-A with A and B blood cells. The sands were tested in indirect antiglobulin tests. Twofold dilutions of anti-D were tested to determine sensitivity.

Iron filings were eliminated from testing because the dark color obscured the red cells. Both sea sands clearly trapped A cells on a column containing Anti-A and allowed the B cells through. After adjustment of centrifugation and column length the sensitivity of the antiglobulin test was found to be comparable to standard manual test results.

The sand samples used in the previous study were soaked in acid cleaning solution (dichromate) overnight. The sands were rinsed in tap water, and then distilled water, and placed in oven to dry. The particles were then examined under a dissecting scope.

Iron filings—all were rough with jagged edges. Particle size varied greatly from about 2 mm to about 200 mm.

Fisher sand—particles from bottle are charged and repelled by a spatula.

Appearance: 100–150 microns average size (some are smaller); clear quartz.

Mallinkrodt sand—more rounded than the Fischer specimens; translucent surface; probably beach tumbled.

Fisher acid-washed sand is tan with dark flecks. Mallinkrodt is much whiter with fewer flecks.

Tested acid washed sand vs sand from the bottles (both labeled "washed") with Bioclone Anti-A™ and preliminary test with Anti-Human serum. The acid washed looked cleaner—no other difference noted—no cells appeared to be bound to sand.

EXAMPLE 4

Addition of High Density Solution:
Coombs Test:

---

Anti-IgG 0.5% PEG, 2% Dextran 87000 MW.
Tested AB serum lot 124B40 - 40 μl
Ortho Antibody Enhancement Solution ™
(low-ionic) lot AES 204-140 - 40 μl
Coombs Control Cell ™ K430

---

Anti-human globulin cells seem to be sticking to sand. Cell button at bottom is somewhat larger with A cell than in the occ.

Tested with beads in normal rabbit serum (NRS) pool and PBS dilutions of normal rabbit serum using Affirmagen™ A cell and OCC cells (IgG coated), in a test tube cartridge.

These were spun in horizontal tabletop centrifuge for 9 minutes, then in a Sorvall GLC 900 RPM for 5 minutes. The matrix appears pink stained. This might be due to non-specific adherence.

Mallinkrodt sea sand with undiluted NRS looked best, as fewer cells adhered to the sand. However, cells are agglutinated by an antibody in the undiluted NRS.

Tested Mallinkrodt sand anti-IgG in 5% PEG K20

2.5% Dextran, ≈20K MW 0.1% gelatin in PBS

| 40 µl serum | controls | serum OAES |
|---|---|---|
| 40 µl OAES | 10 µl cells OAES | 5 µl cells |
| − + | no serum | |
| A cell OCC | + − | + − |
| OCC A cell | OCC A cell | |

A definite difference was observed between + and −. The second two sets were spun 5 minutes in a Sovall GLC at 1000 RPM.

Repeated testing of Mallinkrodt sand. The second two sets 10 mm column

Spin GLC 2000 RPM 5 minutes anti-IgG as before, cells OCC (+) and A (−)

| #1 Control | #2 Test |
|---|---|
| | 40 µl serum |
| 10 µl cells | 40 µl OAES |
| | 10 µl cells |

Results: Positive agglutinated and negative spun-down.

This demonstrates that can separate the serum from the system, and get a positive reaction.

| Tested anti-D diluted in serum - as above in the following dilutions: |
|---|
| 1/100  1/100  1/1000  1/2000  1/4000  0 |

Test results are comparable to conventional anti-human globulin manual testing (indirect Coombs). 1/1000 is a definite positive reaction; 1/2000 looks like agglutination at the bottom of the tube; 1/4000 may be slightly agglutinated; the negative has a rounded button of cells at the bottom of the tube.

The object of this experiment was to determine whether a high density solution such as the dextran albumin solution used in the Simwash Serum/Cell Separation System® would improve the column agglutination antiglobulin test. Anti-IgG was diluted in Simwash® solution and albumin added. Cells coated with IgG were added and cells not coated served as a control.

Results:

The coated cells were agglutinated and trapped by the beads. Some of the uncoated cells bind to the glass beads.

Discussion:

The use of a higher density medium provides a better separation of serum and cells, especially useful in performing Coombs tests.

EXAMPLE 5

Biphasic Centrifugation

The present invention uses nondeformable particles such as glass beads in place of gel filtration media (Sepharose, Sephadex) as used by Lapierre et al. (Transfusion 30:109-113, 1990) and commercialized by Diamed. One particular advantage in the prior art use of such deformable particles, such as gel, is that the ability of the gel to separate particles by size and the translucent quality of the gel makes it a particularly good matrix for agglutinate separation assays. However, the prior art does not avoid certain negative physical problems that are avoided with the present inventions. These physical characteristics include: mechanical fragility, temperature fragility, necessary removal of fines and reagent loss required to swell the gel.

A variety of matrices were evaluated. Desired characteristics were that it be a noncompressible microparticle that would permit separation of agglutinated red cells from unagglutinated red cells, allow easy visualization of the red cells against the matrix, that it be stable (mechanical, temperature, chemical), inert (i.e., not alter or interfere in the serological reaction) and that it be cost effective. Glass beads that are 55–95 microns and acid washed are an example of one type of these particles that fulfill these criteria.

The problem encountered when using the glass beads can best be explained by describing a phenomenon we have termed "sidedness" i.e., the ability to see the red cell agglutinates more clearly when viewed from one side of the cassette (card with 6 reaction chambers) than from the other. Since the glass beads, once packed inside the chamber, are opaque, only red cells (or agglutinates) close to the sides of the chamber are clearly visible. When more agglutinates are visible on one side than another, we refer to this as "sidedness".

This problem may be eliminated by narrowing the chamber so that the thickness of the matrix is reduced. This may be accomplished without reducing the total volume of the chamber by narrowing the diameter of the chamber along one axis and broadening the diameter along the perpendicular axis. Thus, the cross-sectional shape of the chamber is an ellipse, or preferrably a flattened ellipse with two sides parallel to the long axis, rather than a circle. When the chamber is viewed along the shorter dimension, the chamber and matrix are thin enough that red cells and agglutinates on the opposite side are visible.

In centrifugation, if the centrifuge accelerates slowly from standstill to operating speed, this may force the cells to one side of the chamber, with the force of rotation. A faster acceleration, such as five seconds or less, prevents this problem.

Centrifuging in two phases permits the RBCs to be forced together, allowing larger agglutinates to form (as in the tube test) prior to entering the beads. Hence, it is preferred to centrifuge for a period of time and at a speed that allows reactants to contact one another and form larger agglutinates and then at a speed and for a period of time that allows agglutinates to substantially separate from nonagglutinates.

In a test which relies on direct agglutination, such as a blood group, or A/B/O blood typing test, it is especially useful to promote agglutination as much as possible prior to forcing the reactants through the beads. Two phase centrifugation may used to enhance agglutination prior to filtering through the beads. The first phase of centrifugation should be carried at a force and for a duration which will cause maximal contact between cells, but which will not allow significant penetration of the cells into the bead matrix. This first phase may be carried out for approximately two minutes at a centrifugation force of 52–58 g. The centrifuge is then accelerated to force the unagglutinated cells through the bead matrix to the bottom of the chamber. This second phase may be carried out at a force of 191–207 g for approximately three minutes.

K-Resin small cassette format

Jaygo leaded acid washed beads 55–95 μ–7 mm $D_7B_8$ @ 40 ug/ml in CAT Diluent 1

Du Cell and (pg 137) in ORS—10 ul/test

Ortho Centrifuge—2 min @ 15, 3 min @ 1 notch past 30

Results:

| 1 | 2 | 3 | 4 | 5 | 6 | 7 | 8 | 9 | 10 | 11 | 12 |
|---|---|---|---|---|---|---|---|---|----|----|----|
| S | W | O | S | S | S | O | O | O | MS | W  | W  |
| 13 | 14 | 15 | 16 | 17 | 18 | 19 | 20 | 21 | 22 | 20 | 21 |
| M | S | O | MS | O | O | O | controls | | S | | controls |

Comparison of Results DiaMed vs. Ortho BiPhasic (K-Resin)

|    | DiaMed | Ortho BiPhasic |
|----|--------|----------------|
| 1  | M      | S              |
| 2  | O      | W              |
| 3  | 0      | 0              |
| 4  | S      | S              |
| 5  | W      | S              |
| 6  | M      | S              |
| 7  | 0      | 0              |
| 8  | 0      | 0              |
| 9  | 0      | 0              |
| 10 | M      | MS             |
| 11 | W      | W              |
| 12 | VW     | W              |
| 13 | M      | M              |
| 14 | S      | S              |
| 15 | 0      | 0              |
| 16 | W      | MS             |

Conclusion:

Stronger reactions seen in 7/11 positive reactions in BiPhasic Centrifugation

Resins:

K Resin DR03

Dow Polystyrene 67S

Exxon 1024 (Control) Polypropylene

Exxon 105

Eastman Tenite P4CG2-059

All in the new small cassette version

Titer 2K (RKCT 62)

---

A. Dilute 2K 3-fold in AB Serum (ABS 124B)
   13   9   27   81   C
   .3 ml  .6   .3   .6   etc.

Set up in duplicate in C. - 10 min 37° C.

Centrifuge 1 in Diamed .5 min 1375 rpm - centrifuge setting 1 in Ortho-Dupont   2 min  ~500 = 15 – 1
                    3 min ~1600 = 30 + 1

---

1. 40 ul OAES to duplicate cassettes of 5 different resins (Lot ABS 206-1)
2. 10 ul K+RBC (Lot S576 Exp. D 4 Dec 90)
3. 40 ul ABS or Ab dilutions
4. 10 min. 37° C. (Need a Holder for small cassettes in $H_2O$ Bath)

---

| Centri | A - Diamed | 5 min | | 1375 rpm |
|--------|------------|-------|--------|----------|
|        | B - Dupont | 2 min | 15 – 1 | ~500 rpm |
|        |            | 3 min | 30 + 1 | ~1600 rpm |

Interpretation/Comments:

I. Plastics

The clearer the plastic the better/easier to read small agglut/weak reactions. Negative cells OK in all.

Order of clarity.

K-Resin EX 1105 Eastman 059 Ex 1024 (Control Dow PS

II. Centrifugation

The 2-stage centrifugation in Dupont looks good, cells/agglutinates are more evenly dispersed across/through the beads. In Diamed, cells tend to be more on one side than another.

Exception: Eastman. Repeat (in case I centrifuged in centrif. other than what was marked on card) looks like no difference.

Repeat with another AB—use only Dupont Centrif.—1 speed v. 2 speed

---

B. Anti-C (RCST 177)
   2-fold dilutions starting at 1:10
   1:10     30      90      270     810     C
   .3 .6    .3 .6   .3 .6   .3 .6
   90 ul + 890

1. 40 ul OAES
   10 ul RBC $R_1R_1$ 3SS414 18 Dec 90
   40 ul Ab dilutions
   inc 10 mm 37° C.
   Centrif: Dupont    5 min    ~1600 rpm    (30 + 1)
2. Repeat as in 1 stagger incubanus
   Centrif: Dupont    2 min    ~500 rpm     (15 – 1)
                      3 min    ~1600 rpm    (30 + 1)

---

Interpretation:

The difference in centrifugation is not as pronounced in B as in A. However Tube (dilution 3) is slightly clearer in 2-speed centrifugation in the following cassettes: Exxon 1024, Exxon 1105, Dow 2. Continue with more of these, also looking at slow acceleration vs 2-step.

Results:

Titrate 2 c set up in triplicate in 5 different resins and centrifuge 1 speed, 2-speed (slow/fast), and gradual acceleration.

Reagents

---

OAES     AES 206-1
ABS      125A
ANB-C    R0312 Ortho
RBC      $R_2R_2$ 3SS414   18 Dec 90

1. Make 3-fold dilutions of αc starting at 1:10 (see 1853-38)
   .15αc + 1.35 ABS .4 .8 .4 .8 .4 .8 .4 .8 .4 .8 control
   1:10     30      90      270     810     ABS
   1        2       3       4       5       6

*2. Fill cassettes with beads and 40 ul CAT Coombs Diluent
3. Add 40 ul OAES with repeater pipette
4. Add 10 ul RBC
5. Add 40 ul ABS or antibody dilutions
6. Incubate 10 min 37° C.
7. Centrifuge as described below (Dupont)

*(Note: Stagger set A/B/C so that each only incubates 10 minutes)

A = 1 speed notch    30% + 2    ~1750 rpm    5 min
B = 2 speeds         15 + 1     ~500 rpm     2 min
                     30 + 2     ~1750 rpm    3 min -continued

| notches | rpm  | % +/+ notch | |
|---------|------|-------------|---|
| 1       | —    |             |   |
| 2       | —    | 5           |   |
| 3       | 100  | 10 − 1      | 15 sec cups |
| 4       | 300  | 10 + 1      | 15 sec angled |
| 5       | 500  | 15 − 1      | 15 sec |
| 6       | 600  | 15 + 1      | 15 sec cups |
| 7       | 800  | 20 − 1      | 10 sec perpendicular |
| 8       | 950  | 20 + 1      | 10 sec 70 rotor |
| 9       | 1100 | 25 − 1      | 10 sec snaft |
| 10      | 1250 | 25 + 1      | 10 sec |
| 11      | 1400 | 30 − 1      | 10 sec |
| 12      | 1600 | 30 + 1      | 10 sec |
| 13      | 1750 | 30 + 2      | 3 min |

1. Prepare Coombs card in Dow PS (Coombs CAT Dil 4 Dec 90)
2. Add 40 ul OAES + 40 ul ID undil (DEV 90080) or 40 ul AB serum + 10 ul $R_1R_1$ RBC
3. Inc. 5 minutes 37° C.
4. Centrif. 2 min. ~500 rpm (15 + 1) in Dupont. (center slot)
5. Repeat 1-4 centrifuge at 20-1 setting ~800 rpm.

Results:

Majority (>50%) are above beads and centering uniformly into beads.

Agglutinates visible macroscopically in positive chambers.

What is claimed is:

1. A reaction vessel containing a separation region containing a matrix for separating agglutinated cells from unagglutinated cells, and an incubation region, wherein the transverse cross-sectional area of the separation region is elongated along one axis and shortened along the perpendicular axis, thereby permitting increased visibility through the vessel along the shorter axis without decreasing the volumetric capacity of the separation region.

* * * * *

UNITED STATES PATENT AND TRADEMARK OFFICE
Certificate

Patent No. 5,650,068                                          Patented: July 22, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas M. Setcavage and Kathleen J. Reis, both of Milford, N.J.

Signed and Sealed this Twenty-second Day of December, 1998.

WANDA L. WALKER
*Supervisory Patent Examiner*
Art Unit 1723

UNITED STATES PATENT AND TRADEMARK OFFICE
Certificate

Patent No. 5,650,068                                                  Patented: July 22, 1997

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Thomas M. Setcavage and Kathleen J. Reis, both of Milford, NJ.

Signed and Sealed this Nineteenth Day of September, 2000.

WANDA L. WALKER
*Supervisory Patent Examiner*
Art Unit 1723